United States Patent
Zhu et al.

(10) Patent No.: US 7,184,817 B2
(45) Date of Patent: Feb. 27, 2007

(54) SYSTEM AND METHOD FOR ACQUIRING BREATHING PATTERN SIGNALS FROM INTRACARDIAC ELECTROGRAMS AND ITS USE FOR HEART FAILURE THERAPY DECISION MAKING AND DISEASE MONITORING

(75) Inventors: Qingsheng Zhu, Little Canada, MN (US); John Hatlestad, Maplewood, MN (US); Julio Spinelli, Shoreview, MN (US); Ken Kenknight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 403 days.

(21) Appl. No.: 10/742,683

(22) Filed: Dec. 19, 2003

(65) Prior Publication Data

US 2005/0137487 A1    Jun. 23, 2005

(51) Int. Cl.
*A61B 5/402* (2006.01)
(52) U.S. Cl. ............. 600/513; 600/509; 600/484; 607/17; 607/20
(58) Field of Classification Search .......... 607/20, 607/17; 600/513, 509, 484
See application file for complete search history.

(56) References Cited

U.S. PATENT DOCUMENTS

| | | | |
|---|---|---|---|
| 4,719,921 A | 1/1988 | Chirife | 128/419 |
| 4,865,036 A | 9/1989 | Chirife | 128/419 |
| 4,919,136 A * | 4/1990 | Alt | 607/20 |
| 5,139,028 A * | 8/1992 | Steinhaus et al. | 600/510 |
| 5,154,171 A | 10/1992 | Chirife | 128/419 |
| 5,168,869 A | 12/1992 | Chirife | 128/419 |
| 5,174,286 A | 12/1992 | Chirife | 128/419 |
| 5,178,151 A * | 1/1993 | Sackner | 600/485 |
| 5,179,949 A | 1/1993 | Chirife | 128/419 |
| 5,704,356 A * | 1/1998 | Shmueli | 600/407 |
| 5,843,136 A | 12/1998 | Zhu et al. | 607/13 |
| 5,913,308 A * | 6/1999 | Forbes et al. | 600/513 |
| 5,941,903 A | 8/1999 | Zhu et al. | 607/13 |
| 6,119,040 A | 9/2000 | Chirife | 607/18 |
| 6,192,275 B1 | 2/2001 | Zhu et al. | 607/28 |
| 6,226,551 B1 | 5/2001 | Zhu et al. | 607/28 |
| 6,345,204 B1 | 2/2002 | Scheiner et al. | 607/123 |
| 6,415,174 B1 * | 7/2002 | Bebehani et al. | 600/513 |
| 6,449,509 B1 * | 9/2002 | Park et al. | 607/20 |

\* cited by examiner

*Primary Examiner*—Robert Pezzuto
*Assistant Examiner*—Shevon Johnson
(74) *Attorney, Agent, or Firm*—Schwegman, Lundberg, Woessner, & Kluth, P.A.

(57) ABSTRACT

An ICD processing system for acquiring breathing pattern signals from intracardiac electrograms obtained from implantable cardiac devices. The system may include both an implantable ICD device and an external processing system. Both the ICD module and the external processing system processing data to generate a representation for the respiration rate for a patient using intracardiac electrogram data obtained by the ICD device. The ICD module and the external processing module communicate with each other to pass collected patient data from the ICD module to the external processing system. The ICD module and the external processing module process the electrogram data to obtain an processed data representation of the respiration data which is used to estimate the respiration rate.

27 Claims, 9 Drawing Sheets

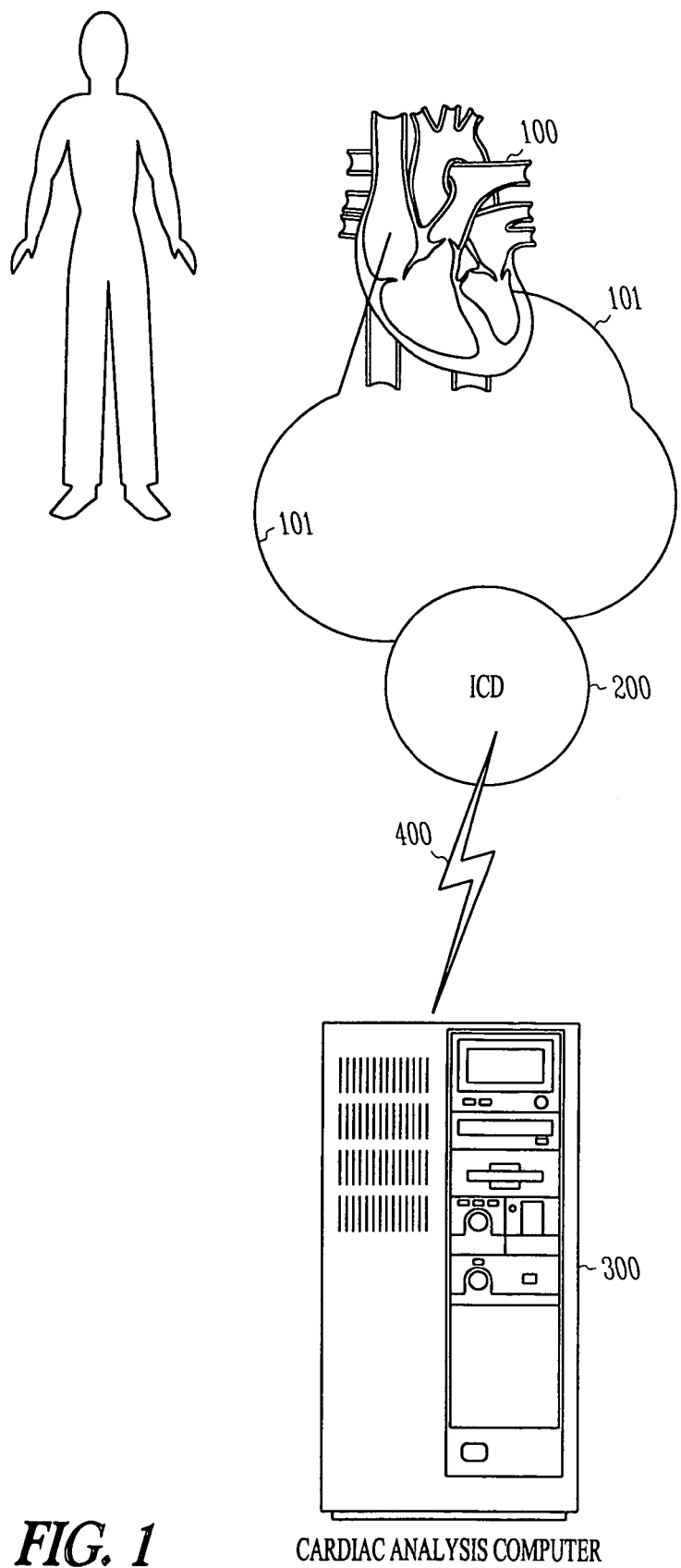
FIG. 1  CARDIAC ANALYSIS COMPUTER

SYSTEM AND METHOD FOR ACQUIRING BREATHING PATTERN SIGNALS FROM INTRACARDIAC ELECTROGRAMS AND ITS USE FOR HEART FAILURE THERAPY DECISION MAKING AND DISEASE MONITORING

TECHNICAL FIELD

This application relates in general to a method, apparatus, and article of manufacture for providing respiration rate estimates from implantable cardiac device data, and more particularly to a method, apparatus, and article of manufacture for acquiring breathing pattern signals from intracardiac electrograms obtained from implantable cardiac devices.

BACKGROUND

Implantable cardiac devices (ICDs) have recently become increasingly commonplace in providing cardiac therapies to patients in need of constant monitoring of heart conditions that require immediate treatment. These ICDs typically provide a single, or at most a few different therapies, to a patient depending upon a small set of observable parameters regarding the condition of a patient's heart. In many situations, the ability to detect addition observable parameters relating to the patient's condition without the introduction of additional interaction will aid in the development of optimal treatment for the patient.

Regardless of the type of cardiac rhythm management device that is employed, all operate to stimulate excitable heart tissue cells adjacent to the electrode of the lead coupled to the rhythm management device. Response to myocardial stimulation or "capture" is a function of the positive and negative charges found in each myocardial cell within the heart. More specifically, the selective permeability of each myocardial cell works to retain potassium and exclude sodium such that, when the cell is at rest, the concentration of sodium ions outside of the cell membrane is approximately equal to the concentration of potassium ions inside the cell membrane. However, the selective permeability also retains other negative particles within the cell membrane such that the inside of the cell membrane is negatively charged with respect to the outside when the cell is at rest.

When a stimulus is applied to the cell membrane, the selective permeability of the cell membrane is disturbed and it can no longer block the inflow of sodium ions from outside the cell membrane. The inflow of sodium ions at the stimulation site causes the adjacent portions of the cell membrane to lose its selective permeability, thereby causing a chain reaction across the cell membrane until the cell interior is flooded with sodium ions. This process, referred to as depolarization, causes the myocardial cell to have a net positive charge due to the inflow of sodium ions. The electrical depolarization of the cell interior causes a mechanical contraction or shortening of the myofibrils of the cell membrane. The syncytial structure of the myocardium will cause the depolarization originating in any one cell to radiate through the entire mass of the heart muscle so that all cells are stimulated for effective pumping. Following heart contraction or systole, the selective permeability of the cell membrane returns and sodium is pumped out until the cell is re-polarized with a negative charge within the cell membrane. This causes the cell membrane to relax and return to the fully extended state, referred to as diastole.

In a normal heart, the sino-atrial (SA) node initiates the myocardial stimulation described above. The SA node comprises a bundle of unique cells disposed within the roof of the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole wherein the atria contract to empty blood into the ventricles. The atrial depolarization from the SA node is detected by the atrioventicular (AV) node which, in turn, communicates the depolarization impulse into the ventricles via the Bundle of His and Purkinje fibers following a brief conduction delay.

In this fashion, ventricular systole lags behind atrial systole such that the blood from the ventricles is pumped through the body and lungs after being filled by the atria. Atrial and ventricular diastole follow wherein the myocardium is re-polarized and the heart muscle relaxes in preparation for the next cardiac cycle. It is when this system fails or functions abnormally that a cardiac rhythm management device may be needed to deliver an electronic pacing stimulus to the heart so as to maintain proper heart rate and synchronization of the filling and contraction of the atrial and ventricular chambers of the heart.

The success of a cardiac rhythm management device in causing a depolarization or evoking a response hinges on whether the energy of the pacing stimulus as delivered to the myocardium exceeds a threshold value. This threshold value, referred to as the capture threshold, represents the amount of electrical energy required to alter the permeability of the myocardial cells to thereby initiate cell depolarization. If the energy of the pacing stimulus does not exceed the capture threshold, then the permeability of the myocardial cells will not be altered and thus no depolarization will result. If, on the other hand, the energy of the pacing stimulus exceeds the capture threshold, then the permeability of the myocardial cells will be altered such that depolarization will result.

Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at a level higher than necessary to effect capture. This can be verified by lowering the stimulation energy level and monitoring for loss of capture at the new energy level.

The ability to detect capture in a cardiac rhythm management device is extremely desirable in that delivering stimulation pulses having energy far in excess of the patient's capture threshold is wasteful of the cardiac rhythm management device's limited power supply. In order to minimize current drain on the power supply, it is desirable to automatically adjust the cardiac rhythm management device such that the amount of stimulation energy delivered to the myocardium is maintained at the lowest level that will reliably capture the heart. To accomplish this, a process known as "capture verification" must be performed wherein the cardiac rhythm management device monitors to determine whether an evoked response or R-wave occurs in the heart following the delivery of each pacing stimulus pulse.

For the most part, prior art implantable cardiac rhythm management devices, including bradycardia and tachycardia pacemakers and cardiac defibrillators, have sense amplifier circuits for amplifying and filtering electrogram signals sensed through electrodes placed in or on the heart and which are coupled by suitable leads to the implantable cardiac rhythm management device. The signals emanating from the sense amplifier are applied to one input of a comparator circuit whose other input is connected to a reference potential. Only when an electrogram signal from the sense amplifier exceeds the reference potential threshold will it be treated as an evoked response. The ability to control the correct receipt of an evoked response signal has evolved and now may be readily distinguished from other signal sources. As a result, the evoked response signal may be used to obtain additional observable parameters of the condition of patient. As discussed above, the respiration of a patient is well known to affect the received evoked response signal. As such, there is a further need for a device to obtain breathing pattern signals from the evoked response signals. These and numerous other disadvantages of the prior art necessitates the need for the method and apparatus provided by the present invention.

SUMMARY

This application relates in general to a method, apparatus, and article of manufacture for acquiring breathing pattern signals from intracardiac electrograms obtained from implantable cardiac devices. One possible embodiment of the present invention is a system method, apparatus, and article of manufacture for acquiring breathing pattern signals from intracardiac electrograms obtained from implantable cardiac devices. The system provides for the acquiring of breathing pattern signals from intracardiac electrograms obtained from implantable cardiac devices. The system includes a cardiac data sample input module for receiving intracardiac electrograms data; a cardiac data over-sampling and filtering module for generating a uniform data rate respiration data signal data from the received intracardiac electrogram data; and a cardiac data resampling module for generating respiration signal data from the uniform data rate respiration data signal data. The respiration signal data represents a signal corresponding to the respiration for a patient.

Another aspect of the present invention is a method and corresponding computer data product for acquiring breathing pattern signals from intracardiac electrograms obtained from implantable cardiac devices. The method obtains peak-to-peak intracardiac electrograms signal data; generates respiration sample data from the peak-to-peak intracardiac electrograms signal data; interpolates the respiration sample data to create a processed respiration signal data having an over-sampled uniform sample rate; low-pass filters the processed respiration signal data to generate a filtered respiration data signal; and sub-samples the filtered respiration data signal at a desired rate to generate an estimated respiration data signal.

BRIEF DESCRIPTION OF THE DRAWINGS

FIG. 1 illustrates an example embodiment of a cardiac ICD system for acquiring breathing pattern signals from intracardiac electrograms obtained from implantable cardiac devices according to one possible embodiment of the present invention.

DETAILED DESCRIPTION

Figure 2A:
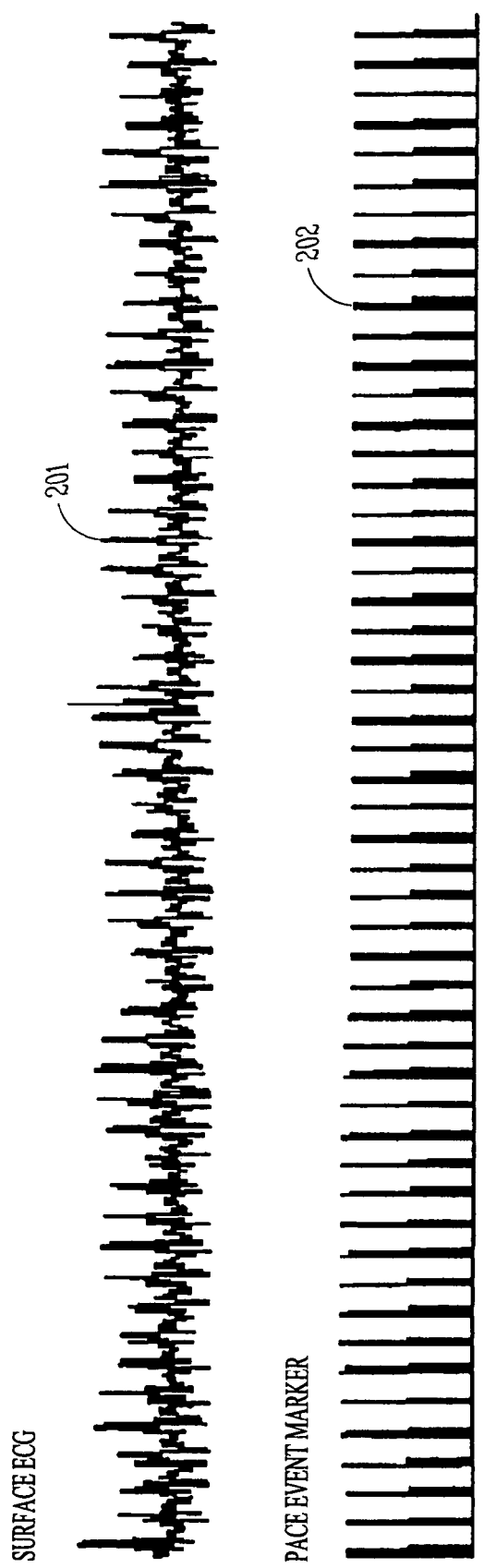
FIG. 2a illustrates an example electrogram signal data according to one possible embodiment of the present invention.

This application relates in general to a method, apparatus, and article of manufacture for acquiring breathing pattern signals from intracardiac electrograms obtained from implantable cardiac devices. In the following detailed description of exemplary embodiments of the invention, reference is made to the accompanied drawings, which form a part hereof, and which is shown by way of illustration, specific exemplary embodiments of which the invention may be practiced. These embodiments are described in sufficient detail to enable those skilled in the art to practice the invention, and it is to be understood that other embodiments may be utilized, and other changes may be made, without departing from the spirit or scope of the present invention. The following detailed description is, therefore, not to be taken in a limiting sense, and the scope of the present invention is defined only by the appended claims.

Throughout the specification and claims, the following terms take the meanings explicitly associated herein, unless the context clearly dictates otherwise. The term "connected" means a direct connection between the items connected, without any intermediate devices. The term "coupled" means either a direct connection between the items connected, or an indirect connection through one or more passive or active intermediary devices. The term "circuit" means either a single component or a multiplicity of components, either active and/or passive, that are coupled together to provide a desired function. The term "signal" means at least one current, voltage, or data signal. Referring to the drawings, like numbers indicate like parts throughout the views.

FIG. 1 illustrates an example embodiment of a cardiac ICD system for acquiring breathing pattern signals from intracardiac electrograms obtained from implantable cardiac devices according to one possible embodiment of the present invention. The cardiac ICD system includes a ICD device 200 electronically connected to a patient's heart 100 using electrical connections 101 to obtain data associated with various observable parameters related to the health of the heart 100 as well as provide medical therapies as needed to maintain a healthy operation for the heart. The ICD device 200 contains electronics to generate electric signals needed to create an evoked response signal in the patient's heart. The ICD device 200 also contains electronics needed to receive and distinguish the evoked response signal from other electrical signals present in the heart. The ICD device 200 contains processing modules as needed to process the received evoked response signal according to embodiments of the present invention.

The ICD device 200 and the cardiac analysis processing system 300 communication over a communications link 400 to provide the cardiac analysis processing system 300 with additional patient's medical history data collected by the ICD device 200 during its operation.

The communications link 400 may consist of any electrical communications link between the processing devices within the pacemaker 200 and the cardiac analysis processing system 300. One skilled in the art will recognize that such a link may be constructed using an RF communications link, an IR communications link, an electrical communications link, an audio based communications link, or any other communications link that provides digital communications between these devices without deviating from the spirit and scope of the present invention as recited within the attached claims.

The use of the communications link 400 permits the data processing modules described herein that may be used in part to implement an embodiment of the present invention to occur either within the ICD device 200 or in the cardiac analysis processing system 300 without deviating from the spirit and scope of the present invention. If the data processing modules are to be present within the ICD device, additional computational resources may be required within the device. These additional computational resources require additional circuitry that may operate at higher processing rates in order to perform these data processing tasks. Both of these factors increase the electrical power consumption for an ICD device 200 that typically operates using a mobile power source such as a battery. As such, these data processing operations may be offloaded to the cardiac analysis processing system 300 when the requirements for the breathing pattern data is not needed in real-time.

However, the breathing pattern data may be useful to determine the heart failure therapy decision making process and the real-time cardiac disease monitoring process that is part of the uses of the ICD device 200. As such, the inclusion of the computational resources needed to perform the data processing of the present invention within the ICD device 200 would permit the real-time use of the data to implement additional cardiac therapies. The trade-off between inclusion of the computational resources within the ICD device 200 and the real-time availability of the processed data signals is a design choice that one skilled in the art will recognize.

FIG. 2a illustrates a set of an example electrogram signal data according to one possible embodiment of the present invention. The signals available to an ICD device 200 according to an embodiment of the present invention include a surface ECG signal 201, a pace event marker signal 202 and an evoked response signal 203. The evoked response signal 203 has been recognized to have its amplitude modulated by a cyclic signal having a frequency suggesting its source is a patient's respiration.

Figure 3:
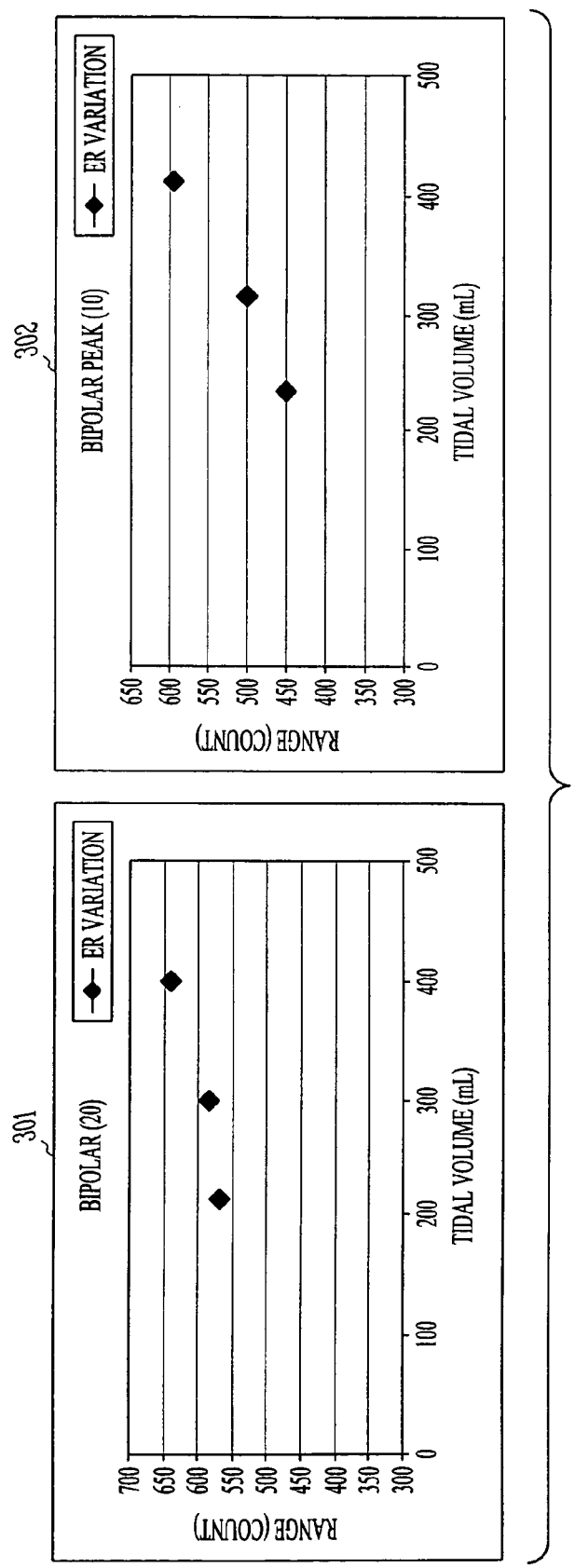
FIG. 3 illustrates results of animal studies relating respiration rate data and tidal volume data to electrogram signals obtained in accordance with the present invention.

Similar phenomena have been observed in many recorded patient study data, however the amplitude of the modulation usually has not been large enough for use. Two separate preliminary animal studies of canines in which the animals were anaesthetized and maintained using inhalation techniques with semi-pressure volume regulated ventilators with isoflurane have been performed. In both of these studies, respiration frequency and tidal volume were set to different levels while an evoked response signal was obtained using an auto-capture system. The results of these studies are illustrated within FIG. 3.

In these results 301–302, an evoked response amplitude variation is illustrated at different tidal volumes. The results in set (A) 301 are obtained at a respiration frequency of 20 cycles/minute. The results in set (B) 302 are obtained at a respiration frequency of 10 cycles/minute. These results suggest a strong correlation between the evoked response amplitude variation and the respiration tidal volume. As such, a process exists to derive an Minute Ventilation (MV) signal using intracardiac electrogram intrinsic and evoked response signals. The derived MV signal may be used to detect onset of Heart Failure (HF) exacerbation and be used to guide HF therapy decisions. Specifically, the derived MV signal may be used to provide an estimate of respiration rate and tidal volume data to characterize patient breathing patterns, and to detect abnormal breathing patterns such as Cheyne-Stokes respiration. The derived MV signal may also be used in conjunction with other information to indicate a need for AV delay re-optimization or high-voltage pacing. In bradycardia patients, the derived MV signal may be used as an input to various adaptation algorithms.

Figure 2B:
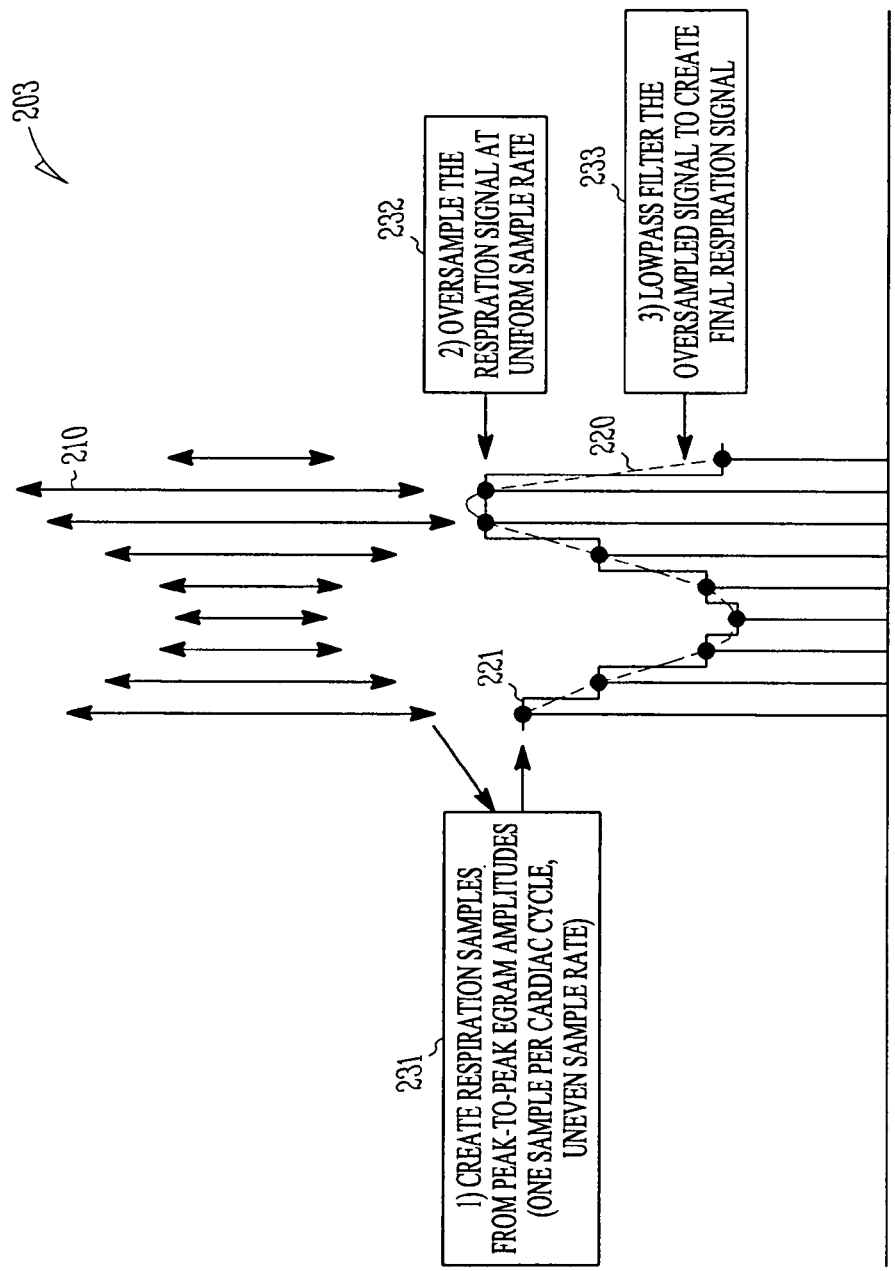
FIG. 2b illustrates an example embodiment of an evoked response signal data used to generate respiration signal data according to one possible embodiment of the present invention.

FIG. 2b illustrates an example embodiment of an evoked response signal data used to generate respiration signal data according to one possible embodiment of the present invention. In FIG. 2b. an evoked response signal 203 is shown with peak-to-peak amplitude values 210 identified. These peak amplitude values are used as input data to extract the modulated respiration signal that is constructed using data points 221 corresponding to the peak-to-peak amplitude values 210.

The respiration signal 220 shows up as a modulation of the amplitude of the evoked response signal 203. The most obvious manifestation of this modulation is that for each cardiac cycle, the peak amplitudes (normally due to the QRS complex) vary over the respiration cycle. Other, less prominent features within the cardiac cycle of the egram are likely modulated in a similar fashion, and may provide alternative or additional sample points for egram modulation. The maximum peak-to-peak amplitudes 210 within each cardiac cycle will be used as the "amplitude" of the respiration 221 during that particular cardiac cycle. One skilled in the art will readily recognize that alternate embodiments may utilize the magnitudes of other identifiable egram features in place of the maximum peak-to-peak amplitudes without deviating from the spirit and scope of the present invention as recited within the attached claims.

Analyzing the egram signal amplitudes 221 for respiration yields one sample (e.g. one QRS amplitude) per cardiac cycle. Since the heart rate of the subject will vary, this implies that the respiration signal will be sampled at a non-uniform rate. For many uses of a respiration waveform, for example for frequency analysis, it is desirable to first convert the non-uniformly sampled respiration waveform to an equivalent signal whose sample points are spaced uniformly in time 231. This requires interpolation of the value of points in the signal between the time points at which the signal was originally "sampled" 232. The topic of time series interpolation has been extensively studied, and is familiar to those versed in the art of signal processing. A number of alternative approaches may be employed based on combined consideration of the required fidelity of the result and the computational resources available to perform the interpolation algorithm.

An embodiment suitable for an application where the fidelity of the respiration signal is important, and available computational resources are sufficient is described below. In this embodiment, the peak-to-peak amplitude 210 within each cardiac cycle forms the respiration signal 220. These values are over sampled 232 at a high rate (for example, at the sample rate of the original egram signal) to form the blue step-wise waveform. This stepwise waveform is then low pass filtered 233 to form the respiration waveform. This low pass-filtered waveform may then be sub sampled at a desired rate, consistent with the Nyquist sampling criterion (i.e. at least twice the frequency of the stopband of the lowpass filter).

In other applications, computational resources may be more limited, and/or fidelity requirements may be less demanding. In such cases, simpler interpolation schemes may prove advantageous. Possibilities range from simple linear or higher order polynomial interpolation, spline interpolation, and interpolation based on a truncated or tapered sine(x)/x kernel. Any of these or other means of time series interpolation may find advantageous application in the context of the present invention.

The waveforms in FIG. 2b represent the typical case, where the heart rate is considerably above the respiration rate. In some circumstances, it is possible that the heart rate and respiration rate can become more comparable. In order for the present invention to provide reasonably accurate respiration readings, there must be (at a minimum) at least two cardiac cycles for each respiration cycle. That is, the heart rate must be at least twice the respiration rate. Thus, in order to increase the usefulness of the present invention, means to identify converging heart rate (HR) and respiration rate (RR) would be advantageous. This could be effected by a number of means, including monitoring the heart rate for bradycardic conditions likely to provide insufficient sample rate for typical respiration rates for the particular patient and assuming the patient starts out with an acceptable HR and RR, monitor the detected respiration rate and identify conditions where the HR/RR ratio approaches an unacceptably low value (with two being the theoretical minimum). In conditions where the HR/RR ratio is deemed insufficient for accurate respiration monitoring, reporting of the respiration signal would be suspended to avoid presenting false readings.

Figure 4:
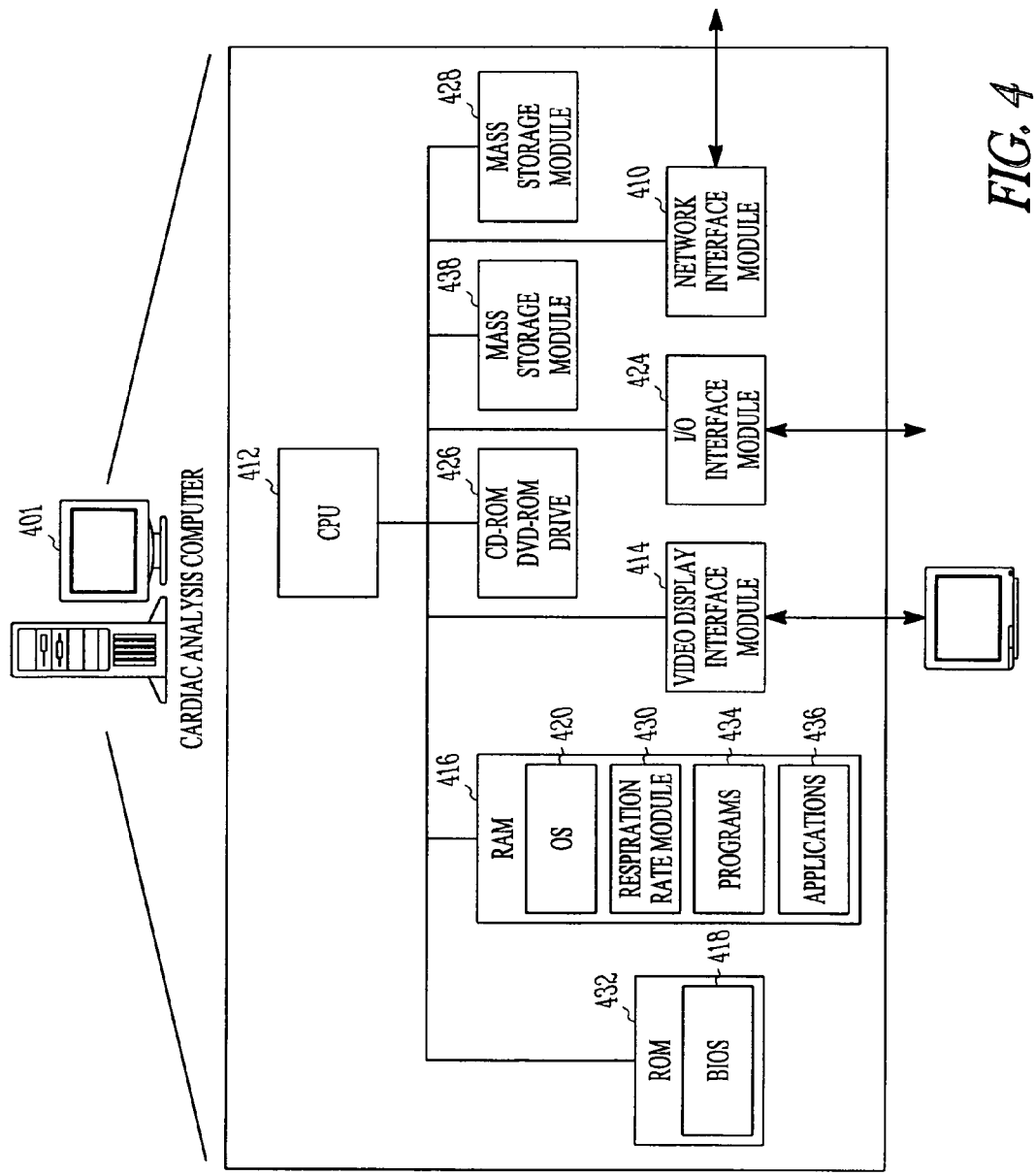
FIG. 4 illustrates a computing system that may be used to construct various computing systems that may be part of a distributed processing and communications system according to one embodiment of the present invention.

FIG. 4 illustrates a computing system that may be used to construct various computing systems that may be part of a distributed processing and communications system according to one embodiment of the present invention. In an exemplary embodiment of a cardiac analysis processing system 401, computing system 401 is operative to provide a cardiac analysis processing system. Those of ordinary skill in the art will appreciate that the cardiac analysis processing system 401 may include many more components than those shown with reference to a computing system 300 shown in FIG. 4. However, the components shown are sufficient to disclose an illustrative embodiment for practicing the present invention. As shown in FIG. 1, cardiac analysis processing system 300 is connected to a ICD device 200, or other devices as needed. Those of ordinary skill in the art will appreciate that a network interface unit 410 includes the necessary circuitry for connecting cardiac analysis processing system 401 to a network of other computing systems, and is constructed for use with various communication protocols including the TCP/IP protocol. Typically, network interface unit 410 is a card contained within neural network training and data collection system.

Cardiac analysis processing system 401 also includes processing unit 412, video display adapter 414, and a mass memory 416, all connected via bus 422. The mass memory generally includes RAM 416, ROM 432, and one or more permanent mass storage devices, such as hard disk drive 428, a tape drive, CD-ROM/DVD-ROM drive 426, and/or a floppy disk drive. The mass memory stores operating system 420 for controlling the operation of cardiac analysis processing system 400. It will be appreciated that this component may comprise a general purpose server operating system as is known to those of ordinary skill in the art, such as UNIX, MAC OS™, LINUX™, or Microsoft WINDOWS NT®. Basic input/output system ("BIOS") 418 is also provided for controlling the low-level operation of processing system 401.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The mass memory also stores program code and data for providing a software development and neural network analysis and training system. More specifically, the mass memory stores applications including respiration rate program 430, programs 434, and similar analysis tool applications 436. Respiration Signal processing program 430 includes computer executable instructions which, when executed by computer 401 perform the logic described herein.

Figure 6:
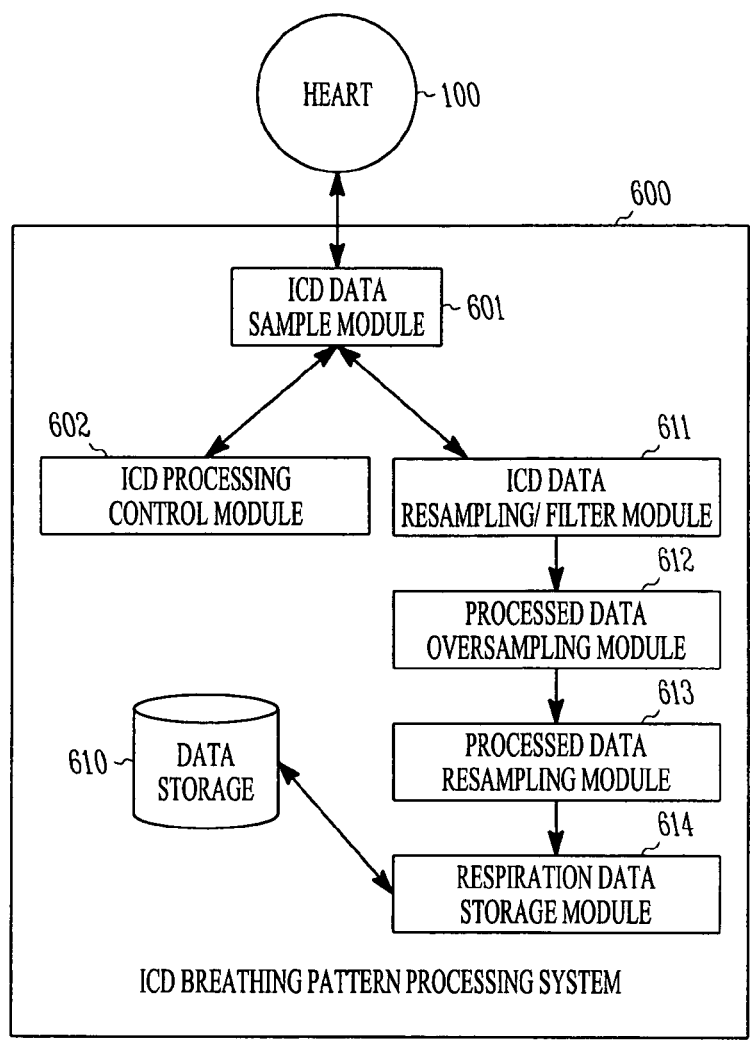
FIG. 6 illustrates another example embodiment of an ICD breathing pattern processing module for use with a cardiac ICD device according to one possible embodiment of the present invention.

Cardiac analysis processing system 401 also comprises input/output interface 424 for communicating with external devices, such as a mouse, keyboard, scanner, or other input devices not shown in FIG. 4. Likewise, cardiac analysis processing system 401 may further comprise additional mass storage facilities such as CD-ROM/DVD-ROM drive 426 and hard disk drive 428. Hard disk drive 428 is utilized by cardiac analysis processing system 400 to store, among other things, application programs, databases, and program data used by cardiac analysis processing system application program 430. The operation and implementation of these databases is well known to those skilled in the art. FIG. 6 illustrates an example embodiment of a cardiac ICD device module that is part of an a cardiac ICD system for acquiring breathing pattern signals from intracardiac electrograms obtained from implantable cardiac devices according to one possible embodiment of the present invention.

Figure 5:
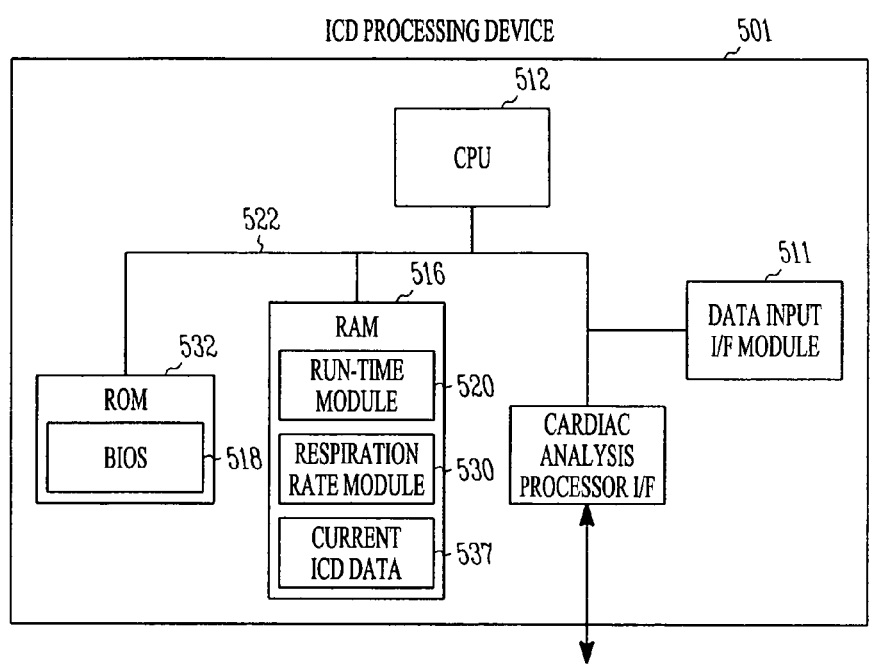
FIG. 5 illustrates a computing system that may be used to construct a cardiac ICD module according to another example embodiment of the present invention.

FIG. 5 illustrates a computing system that may be used to construct a cardiac ICD module according to another example embodiment of the present invention. One skilled in the art will recognize the processing system 500 to represent a reduced set of modules shown in FIG. 4 that are suitable for creation of an embedded processing system. Because the embedded processing system does not possess most of the peripheral devices typically contained within a general purpose computing system illustrated within FIG. 4, the embedded processing system 500 includes a CPU module 512 connected to a system bus that permits communication with RAM 516, ROM 532, a cardiac analysis processor interface module 510 and a cardiac data input interface module 511. Within the RAM 516 and 532, a reduced set of programmable processing modules are stored. Typically these modules represent the minimal set of data processing modules needed to implement the ICD processing device 500. In addition, the operating system typically found as part of a general purpose computing system 401 is replaced with a run-time module 520 that performs the set of processing functions needed within the ICD processing device 500.

The two interface modules, the cardiac analysis processor interface module 510 and a cardiac data input interface module 511 are used to obtain cardiac electrogram data and to communicate with a remote cardiac analysis processing system 300 as needed. Interaction with other processing modules and therapy devices would typically require a similar interface module.

FIG. 6 illustrates another example embodiment of an ICD breathing pattern processing module for use with a cardiac ICD device according to one possible embodiment of the present invention. The cardiac analysis processing system 600 receives collected patient data from the ICD device 200 through an ICD interface module 601 for use by a set of data processing modules. These data processing modules include an ICD data resampling and filtering module 611, a processed data over-sampling module 612, a processed data re-sampling module 613, and a respiration data storage module 614. The ICD data resampling and filtering module 611 performs the first portion of the processing in which the non-uniform sampled data is resampled at a uniform sampling rate and then subsequently low-pass filtered as described in detail above with respect to FIGS. 2a and 2b. The processed data over-sampling module 612 is used to generate the high sample data rate respiration signal as described in detail above with respect to FIGS. 2a and 2b. The processed data re-sampling module 613 resamples the data at a desired data rate for use in subsequent processing or storage within a data storage area 610 through a respiration data storage interface module 614.

Figure 7:
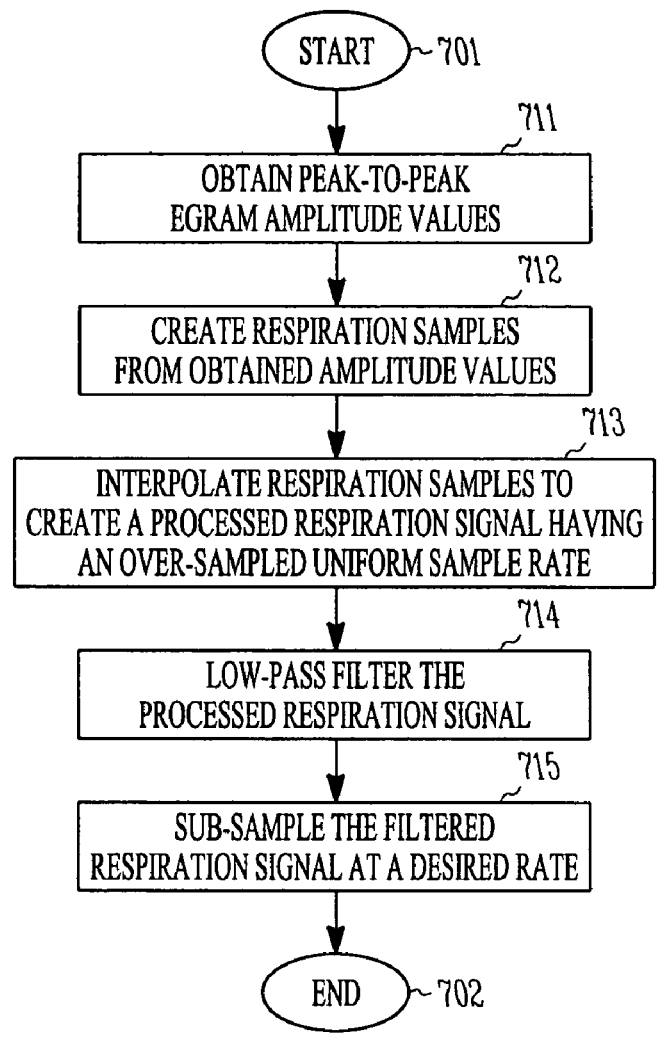
FIG. 7 illustrates an example operation flow for a cardiac ICD system for acquiring breathing pattern signals from intracardiac electrograms obtained from an implantable cardiac device according to one possible embodiment of the present invention.

FIG. 7 illustrates an example operation flow for a cardiac ICD system for acquiring breathing pattern signals from intracardiac electrograms obtained from implantable cardiac devices according to one possible embodiment of the present invention. The processing starts 701 and the processing obtains peak-to-peak egram amplitude values in module 711. Using this obtained amplitude value data, respiration sample signals are created in module 712. Module 713 interpolates the respiration sample data values to create a processed respiration signal having a high-sample rate or over-sampled uniform sample rate. The over-sampled uniform sample rate respiration signal is then low-pass filtered in module 714 before it is sub-sampled in module 715 to generate a filtered respiration signal. As discussed above, the filtered respiration signal may be used to estimate respiration rate and tidal volume as discussed above in more detail as the processing ends 702.

Figure 8:
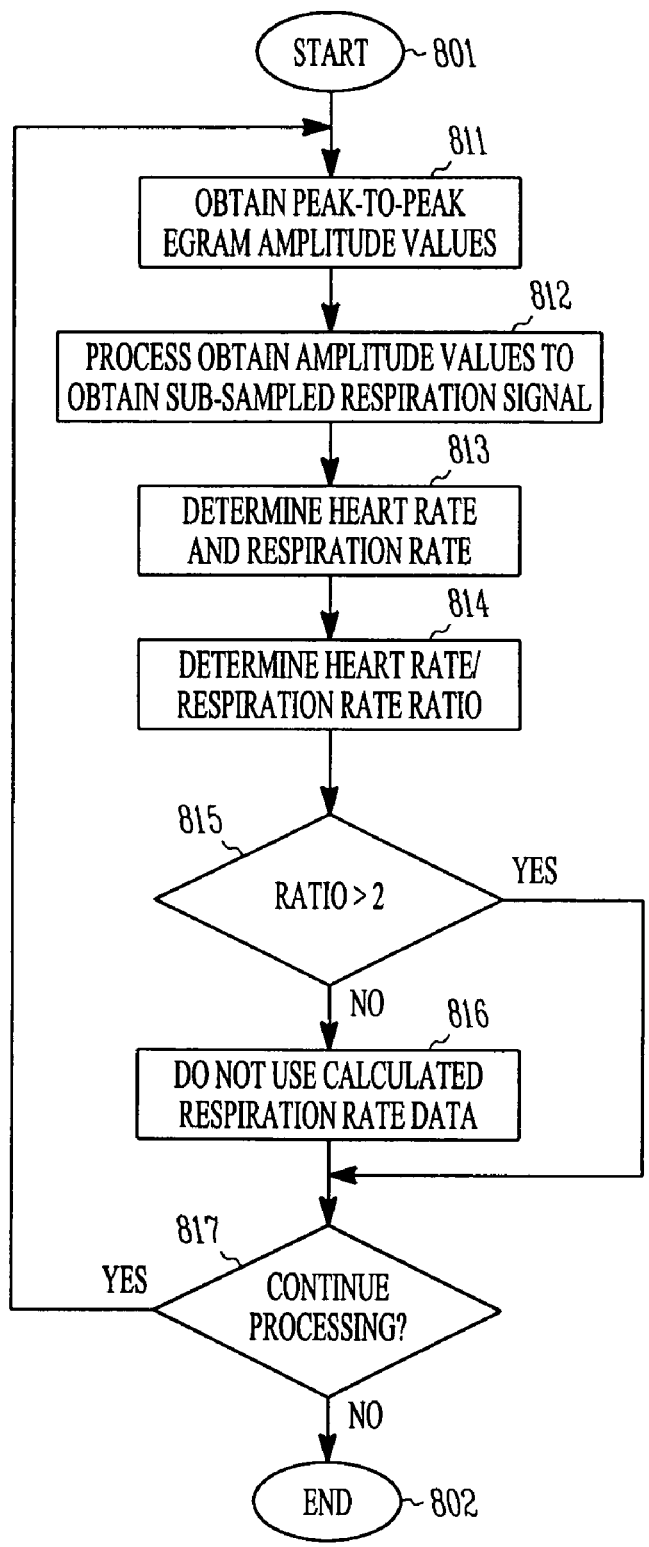
FIG. 8 illustrates another example operation flow for a cardiac ICD system for acquiring breathing pattern signals from intracardiac electrograms obtained from implantable cardiac devices according to one possible embodiment of the present invention.

FIG. 8 illustrates another example operation flow for a cardiac ICD system for acquiring breathing pattern signals from intracardiac electrograms obtained from implantable cardiac devices according to one possible embodiment of the present invention. The processing starts 801 and the processing obtains peak-to-peak egram amplitude values in module 811. Using this obtained amplitude value data, the filtered respiration signal are created in module 812. Module 813 uses the filtered respiration signal and the original peak-to-peak amplitude signal to estimate heart rate and respiration rate. As discussed above, the respiration rate must be twice the estimated heart rate in order for the estimate of the respiration rate to be accurate. As such, module 814 determines the ratio of heart rate to respiration rate. Test module 815 determines if the calculated ration is greater than 2. If the test module 815 determines the ratio is greater than 2, the processing continues to test module 817. If the test module 815 determines the ratio is not greater than 2, the processing continues to module 816 in which the data is identified as data that should not be used before proceeding to test module 817. Test module 817 determines with additional processing is to occur. If so, the processing continues to module 811 and the above processing repeats. If the processing is not to continue, the processing ends 802.

FIG. 5 illustrates an example of a suitable operating environment in which the invention may be implemented. The operating environment is only one example of a suitable operating environment and is not intended to suggest any limitation as to the scope of use or functionality of the invention. Other well known computing systems, environments, and/or configurations that may be suitable for use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like.

The invention may also be described in the general context of computer-executable instructions, such as program modules, executed by one or more computers or other devices. Generally, program modules include routines, programs, objects, components, data structures, etc. that perform particular tasks or implement particular abstract data types. Typically the functionality of the program modules may be combined or distributed in desired in various embodiments.

Processing devices attached to a communications network typically includes at least some form of computer readable media. Computer readable media can be any available media that can be accessed by these devices. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by processing devices.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Additionally, the embodiments described herein are implemented as logical operations performed by a programmable processing devices. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

While the above embodiments of the present invention describe a cardiac ICD system for acquiring breathing pattern signals from intracardiac electrograms obtained from implantable cardiac devices, one skilled in the art will recognize that the use of a particular computing architecture for a data processing system are merely example embodiments of the present invention. It is to be understood that other embodiments may be utilized and operational changes may be made without departing from the scope of the present invention as recited in the attached claims.

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a method, apparatus, and article of manufacture a cardiac ICD system for acquiring breathing pattern signals from intracardiac electrograms obtained from an implantable cardiac device.

What is claimed is:

1. A system comprising:
    a cardiac data sample input module for receiving intracardiac electrogram data including cardiac depolarizations;
    a cardiac data over-sampling and filtering module for generating a uniform data rate respiration data signal data from amplitudes of the depolarizations of the received intracardiac electrogram data;
    a cardiac data resampling module for generating respiration signal data from the uniform data rate respiration data signal data;
    wherein the respiration signal data represents a signal corresponding to the respiration for a patient.

2. The system according to claim 1, wherein the intracardiac electrogram data corresponds to a non-uniform sampled signal.

3. The system according to claim 2, wherein the cardiac data over-sampling and filtering module interpolates the received intracardiac electrogram data to generate a uniform rate data signal.

4. The system according to claim 3, wherein the cardiac data over-sampling and filtering module further low-pass filters the uniform rate data signal to generate the uniform data rate respiration data signal.

5. The system according to claim 2, wherein the cardiac data resampling module resamples the uniform data rate respiration data signal at a desired data rate.

6. The system according to claim 2, wherein the respiration signal data is used to provide an estimate for the respiration rate of a patient.

7. The system according to claim 6, wherein the respiration signal data is used to provide an estimate for the respiration tidal volume of a patient.

8. The system according to claim 1, wherein the cardiac data over-sampling and filtering module and the cardiac data resampling module are located within an implantable cardiac device.

9. The system according to claim 2, wherein the cardiac data over-sampling and filtering module and the cardiac data resampling module are located within a cardiac analysis processing system.

10. The system according to claim 2, wherein the respiration signal data is stored within a data storage module for subsequent use.

11. A method comprising:
    obtaining peak-to-peak intracardiac electrogram signal data;
    generating respiration sample data from amplitudes of depolarizations in the peak-to-peak intracardiac electrogram signal data;
    interpolating the respiration sample data to create a processed respiration signal data having an over-sampled uniform sample rate;
    low-pass filtering the processed respiration signal data to generate a filtered respiration data signal; and
    sub-sampling the filtered respiration data signal at a desired rate to generate an estimated respiration data signal.

12. The method according to claim 11, wherein the method further comprises:
    generating a estimated respiration rate and estimated respiration tidal volume from the estimated respiration signal.

13. The method according to claim 12, wherein the method further comprises:
    generating a estimated heart rate and an estimated heart rate/respiration rate ratio; and
    using the estimated respiration signal when the estimated heart rate/respiration rate ratio is greater than 2.

14. A computer data product containing computer readable data encoding instructions for implementing a computer implemented method comprising:
    obtaining peak-to-peak intracardiac electrogram signal data;
    generating respiration sample data from amplitudes of depolarizations in the peak-to-peak intracardiac electrogram signal data;
    interpolating the respiration sample data to create a processed respiration signal data having an over-sampled uniform sample rate;
    low-pass filtering the processed respiration signal data to generate a filtered respiration data signal; and
    sub-sampling the filtered respiration data signal at a desired rate to generate an estimated respiration data signal.

15. The computer data product according to claim 14, wherein the method further comprises:
    generating a estimated respiration rate and estimated respiration tidal volume from the estimated respiration signal.

16. The computer data product according to claim 15, wherein the method further comprises:
   generating a estimated heart rate and an estimated heart rate/respiration rate ratio; and
   using the estimated respiration signal when the estimated heart rate/respiration rate ratio is greater than 2.

17. A system providing acquiring breathing pattern signals from intracardiac electrograms obtained from implantable cardiac devices, the system comprising:
   a cardiac data sample input module for receiving intracardiac electrograms data, wherein the intracardiac electrograms data corresponds to a non-uniform sampled signal;
   a cardiac data over-sampling and filtering module for generating a uniform data rate respiration data signal data from the received intracardiac electrogram data;
   a cardiac data resampling module for generating respiration signal data from the uniform data rate respiration data signal data;
   wherein the respiration signal data represents a signal corresponding to the respiration for a patient and wherein the respiration signal data is used to provide an estimate for the respiration rate of a patient.

18. The system according to claim 17, wherein the respiration signal data is used to provide an estimate for the respiration tidal volume of a patient.

19. A method for acquiring breathing pattern signals from intracardiac electrograms obtained from implantable cardiac devices, the method comprising:
   obtaining peak-to-peak intracardiac electrograms signal data;
   generating respiration sample data from the peak-to-peak intracardiac electrograms signal data;
   interpolating the respiration sample data to create a processed respiration signal data having an over-sampled uniform sample rate;
   low-pass filtering the processed respiration signal data to generate a filtered respiration data signal; and
   sub-sampling the filtered respiration data signal at a desired rate to generate an estimated respiration data signal; and
   generating a estimated respiration rate and estimated respiration tidal volume from the estimated respiration sign.

20. The method according to claim 19, wherein the method further comprises:
   generating a estimated heart rate and an estimated heart rate/respiration rate ratio; and
   using the estimated respiration signal when the estimated heart rate/respiration rate ratio is greater than 2.

21. A computer data product containing computer readable data encoding instructions for implementing a computer implemented method for acquiring breathing pattern signals from intracardiac electrograms obtained from implantable cardiac devices, the method comprising:
   obtaining peak-to-peak intracardiac electrograms signal data;
   generating respiration sample data from the peak-to-peak intracardiac electrograms signal data;
   interpolating the respiration sample data to create a processed respiration signal data having an over-sampled uniform sample rate;
   low-pass filtering the processed respiration signal data to generate a filtered respiration data signal;
   sub-sampling the filtered respiration data signal at a desired rate to generate an estimated respiration data signal; and
   generating a estimated respiration rate and estimated respiration tidal volume from the estimated respiration signal.

22. The computer data product according to claim 20, wherein the method further comprises:
   generating a estimated heart rate and an estimated heart rate/respiration rate ratio; and
   using the estimated respiration signal when the estimated heart rate/respiration rate ratio is greater than 2.

23. A method comprising:
   obtaining an electrogram signal from implanted electrodes;
   measuring peak depolarization amplitudes of the electrogram signal; and
   using the peak depolarization amplitudes to form a first respiration signal.

24. The method of claim 23, comprising interpolating between the peak depolarization amplitudes of the first respiration signal to form a second respiration signal.

25. The method of claim 24, comprising lowpass filtering the second respiration signal to form a third respiration signal.

26. The method of claim 25, comprising sampling the third respiration signal to form a fourth respiration signal.

27. The method of claim 26, in which the acts of obtaining, measuring, using the peak depolarization amplitudes to form a first respiration signal, interpolating, lowpass filtering, and sampling are carried out using an implantable medical device.

* * * * *

UNITED STATES PATENT AND TRADEMARK OFFICE
CERTIFICATE OF CORRECTION

PATENT NO. : 7,184,817 B2 Page 1 of 1
APPLICATION NO. : 10/742683
DATED : February 27, 2007
INVENTOR(S) : Zhu et al.

It is certified that error appears in the above-identified patent and that said Letters Patent is hereby corrected as shown below:

In column 13, line 44, in Claim 19, delete "sign" and insert -- signal --, therefor.

Signed and Sealed this

Twenty-fourth Day of June, 2008

JON W. DUDAS
*Director of the United States Patent and Trademark Office*